United States Patent [19]

Moreau

[11] 4,085,922

[45] Apr. 25, 1978

[54] METHOD AND APPARATUS FOR CONTINUOUSLY MEASURING THE ANNEALING LEVEL ON WIRES OR STRIPS

[75] Inventor: Marc Moreau, Asnieres, France

[73] Assignee: Trefimetaux, Paris, France

[21] Appl. No.: 758,831

[22] Filed: Jan. 12, 1977

Related U.S. Application Data

[62] Division of Ser. No. 691,608, Jun. 1, 1976.

[30] Foreign Application Priority Data

Jun. 6, 1975 France .............................. 75 18328

[51] Int. Cl.$^2$ .............................................. C21D 9/64
[52] U.S. Cl. ...................................... 266/90; 266/92; 148/12 B; 266/102; 266/104
[58] Field of Search ................. 148/12 B, 128; 266/80, 266/90, 92, 102, 104

[56] References Cited

U.S. PATENT DOCUMENTS

| | | | |
|---|---|---|---|
| 2,897,698 | 8/1959 | Van Ormer ........................ | 266/90 X |
| 3,708,354 | 1/1973 | Rowell .............................. | 266/99 X |

FOREIGN PATENT DOCUMENTS 2,206,000  5/1974  France ................................... 266/90

*Primary Examiner*—Roy Lake
*Assistant Examiner*—Paul A. Bell
*Attorney, Agent, or Firm*—Dennison, Dennison, Meserole & Pollack

[57] ABSTRACT

In a method and apparatus for continuously measuring the annealing level on wires or strips, a wire or strip is passed, in a continuous feed, over a pulley of small diameter, at a tension less than that corresponding to the elastic limit of the material of which the wire or strip is made, so as to produce permanent elongation of 0.1 to 1%, this elongation being taken as a measurement of the annealing level, and utilized to control the annealing level.

12 Claims, 6 Drawing Figures

METHOD AND APPARATUS FOR CONTINUOUSLY MEASURING THE ANNEALING LEVEL ON WIRES OR STRIPS

This is a division of application Ser. No. 691,608, filed June 1, 1976.

The invention concerns a method and apparatus for continuously measuring the annealing level on wires or strips.

It applies more particularly to wires and strips made of aluminum or an aluminum alloy, copper or a copper alloy or stainless steel.

The mechanical testing methods normally used to ascertain the mechanical properties, such as the elastic limit or modulus of elasticity of a wire or strip, consist of taking one or more samples of the product for testing. This procedure has the advantage of enabling accurate testing apparatus to be used, operating independently of the production line.

On the other hand it has a certain number of disadvantages:

— only samples are tested, while the greater part of the production remains unchecked;
— during the phase when the production line is adjusted, it is necessary to stop the line so that a sample can be taken, to await the result of checking then to correct the adjustments, check for a second time with the line stopped again, and so on until the desired properties are finally obtained by trial and error;
— in cases where the production line deviates from the adjustments during operation, the manufactured product becomes incorrect until the defect is revealed by the next sample check; this sometimes means that large quantities of the product are wasted;
— finally, short-term changes in the adjustment parameters, occurring between two samplings as a result of variations in the environment, e.g. in the voltage of the mains electricity, the flow rate of the heat exchanging fluids or in room temperature, may make some parts of the manufactured product incorrect without this being revealed by the checking facilities.

These disadvantages show the importance of having continuous testing means installed on the production line, instantaneously delivering a measured value which represents the desired mechanical properties.

For example, insulated conductive wires which are used for transmitting telephone calls have a conductive metal core comprising a copper or aluminum wire which has undergone annealing treatment. It is advantageous to anneal such wires continuously by the Joule effect in an appropriate annealing oven. In the oven the electric current passes through the wire to bring it to the desired annealing temperature, and it is then necessary for the intensity of the current to be accurately adjusted since it determines the metallurgical structure obtained. The current intensity is said to result in a given "annealing level".

Certain mechanical properties depend on the annealing level, particularly the elasticity of the wire in the field of slight permanent deformations; these properties in turn determine the quality of the component telephone cables known as "quartes", which are assembled to form a telephone cable. If the "quartes" obtained are to be of high quality it is thus essential for the degree of annealing to be controlled permanently and accurately, in order that the desired annealing level can be obtained regularly and continuously.

The optimum value for the intensity of the annealing current is not known exactly a priori since it depends, for a given annealing oven, on the speed at which the wire passes through, its cross-section, its composition and metallurgical history, its initial temperature, on heat exchanges between the moving wire and its environment such as air, water vapor and guiding pulleys and on heat losses by radiation.

The installations used generally have an arrangement for regulating the intensity of the annealing current as a function of the speed at which the wire passes through; this is based on an approximate evaluation and a priori on the law which must link these two values to maintain a constant annealing level when the speed of the wire varies. This current intensity value is determined by trial and error, resulting in wasting of time, wasting of metal during testing and, above all, in the impossibility of detecting and correcting any changes in the annealing level obtained, due to fluctuations in the above-mentioned factors, while the production line is operating.

The absence of any testing during operation is the reason why many manufactures are rejected as having an incorrect annealing level. The lack of such testing becomes particularly troublesome in cases where aluminum is annealed continuously; here the intensity of the annealing current has to be adjusted very accurately.

This shows the importance of an arrangement which is placed right at the outlet of the annealing oven and which transmits an electric signal conveying the annealing level actually obtained on the wire and, more specifically, conveying the mechanical properties of the metal in the field of slight permanent deformations.

An arrangement of this type is known from French Pat. No. 2,206,000 in the name of "Leonische Drahtwerke AG". It comprises two capstans which are rigidly connected and co-axial, of slightly different diameters D and $d$, the ratio $D/d$ being e.g. 1.005/1. The wire is wound first over the capstan of smaller diameter $d$, then diverted onto a dynamometric pulley before being wound over the capstan of larger diameter D. In the continuous advancing movement the wire is elongated, between the two capstans, in the ratio $D/d = 1.005/1$. This elongation is associated with a tensile stress which depends particularly on the metallurgical state of the wire and, more particularly, on its annealing level.

The arrangement has the following disadvantages:

— the wire is already taut on entering the measuring apparatus and the initial tension is added to the tension of 0.05% applied by passage over the two pulleys; this is a first cause of error in measurement;
— a second cause of error stems from the possibility that the wire may creep over the capstans; the mechanical tension of the wire on either side of a capstan is in fact very different: in the measuring zone the tension exceeds the elastic limit of the wire, whereas on either side of the measuring apparatus tension is far lower in order to avoid the danger of untimely elongation of the wire; the wire is wound over the capstans at an angle which generally cannot exceed about 270°.

In practice, when the wire is properly annealed and thereby properly degreased, provided that the tension of the wire on either side of the apparatus is stable and sufficiently high, there will be little creep over the capstans. However, this is not so if these conditions are not fulfilled. For example, with a copper wire which has been cold-drawn or insufficiently annealed, considerable creeping may take place and the reading would then correspond to a more annealed state than is actually the case, in which the wire sets up little resistance to elongation. The reading is thus reversed and, if the apparatus is used in automatic regulation to control the annealing level, it will initiate a drop in the electric annealing current, thus tending to increase the error.

The subject matter of the invention involves a method of and apparatus for continuously measuring the annealing level on wires or strips in a manner so as to remedy the above disadvantages.

In the method of the invention the wire or strip is passed in a continuous advancing movement over a pulley of small diameter, at a tension lower than that corresponding to the elastic limit of the material from which the wire or strip is made, the diameter of the pulley and the tension being selected so that such passage produces a permenent elongation of the wire or strip by 0.1 to 1%, and the permanent elongation is taken as a measuring value, representing the mechanical properties of the wire and, more particularly, its annealing level.

The apparatus according to the invention comprises an upstream capstan and a downstream capstan. A loose pulley of small diameter is arranged between the two capstans and mounted at the free end of an arm adapted to rock about a shaft. The arm is equipped with a means of applying a force F to it, such as a weight hung over it, and with a position detector controlling a means for adjusting the rotary speed of one of the capstans. A computer enables the relative difference $\Delta v/v$ between the speeds of the two capstans to be ascertained. The wire passes successively over the upstream capstan, the pulley of small diameter and the downstream capstan.

The invention thus defined is explained with reference to examples illustrated by the accompanying drawings. In the drawings.

Figure 2:
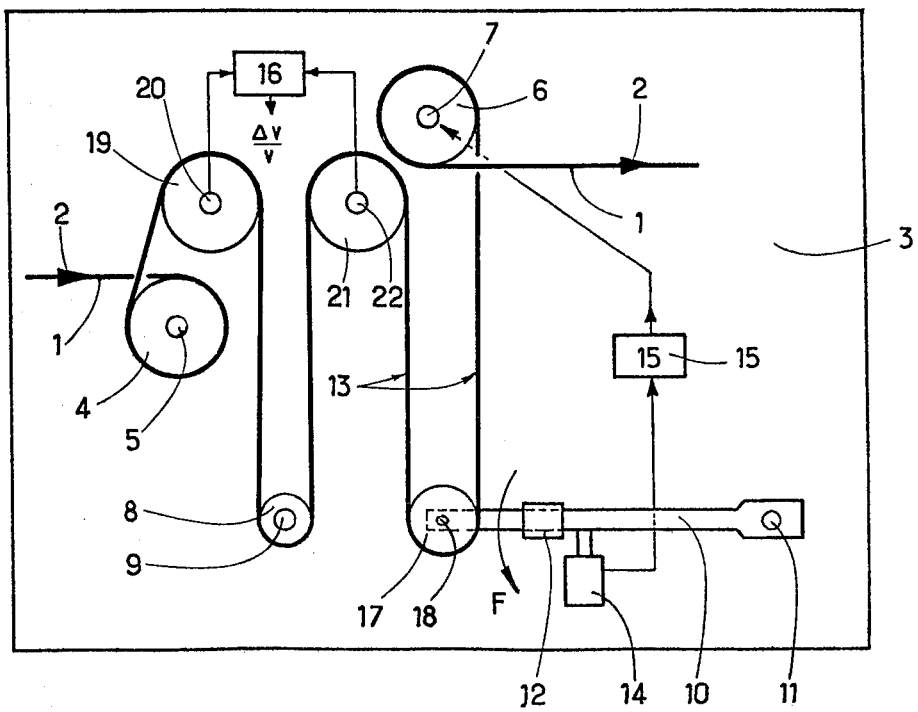
Figure 5:
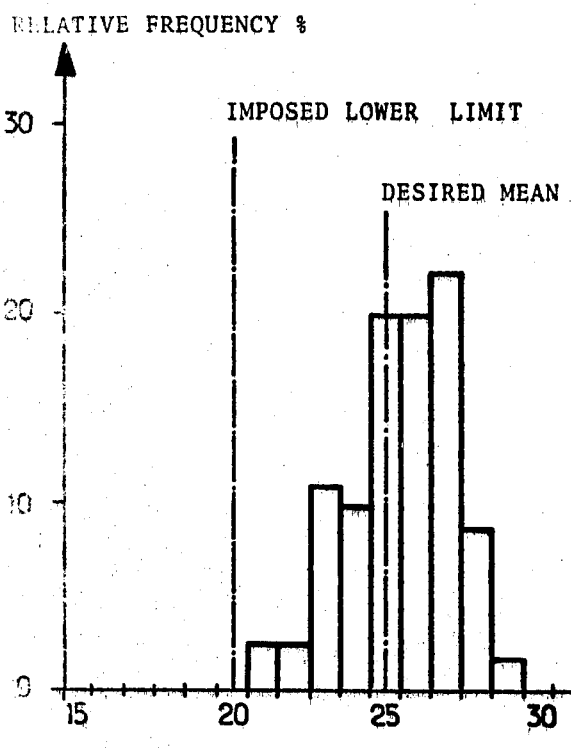
Figure 6:
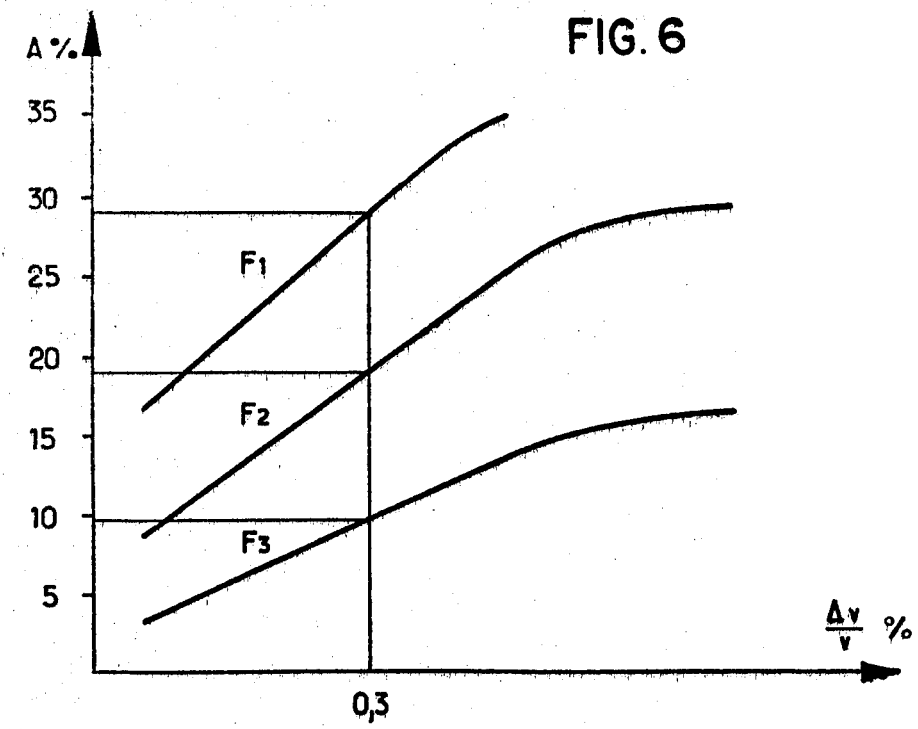

FIG. 5 is a histogram of the results obtained relating to elongations at rupture A%, and FIG. 6 shows the curves for elongation at rupture A% measured on continuously annealed samples of copper wire 0.8 mm in diameter, as a function of the ratio $\Delta v/v$, the relative difference in speed between the measuring pulleys of the FIG. 2 apparatus, for three increasing values F1, F2, and F3 of the load applied to the rocking arm.

In these figures identical components carry identical references.

The method of continuously measuring the annealing level of wires or strips is based on the fact that a metal wire which has been annealed to a greater or less degree is liable to slight permanent elongation when it passes over a pulley of small diameter, at a mechanical tension which is constant and below its elastic limit. This permanent elongation is the measuring value which represents the mechanical properties of the wire of strip and, more particularly, its annealing level.

The tension applied to the wire and the diameter of the pulley are selected to give an elongation of 0.1 to 1%. In practice, the diameter of the pulley is generally from 20 to 500 and preferably from 30 to 200 times the diameter of the wire or the thickness of the strip.

Figure 1:
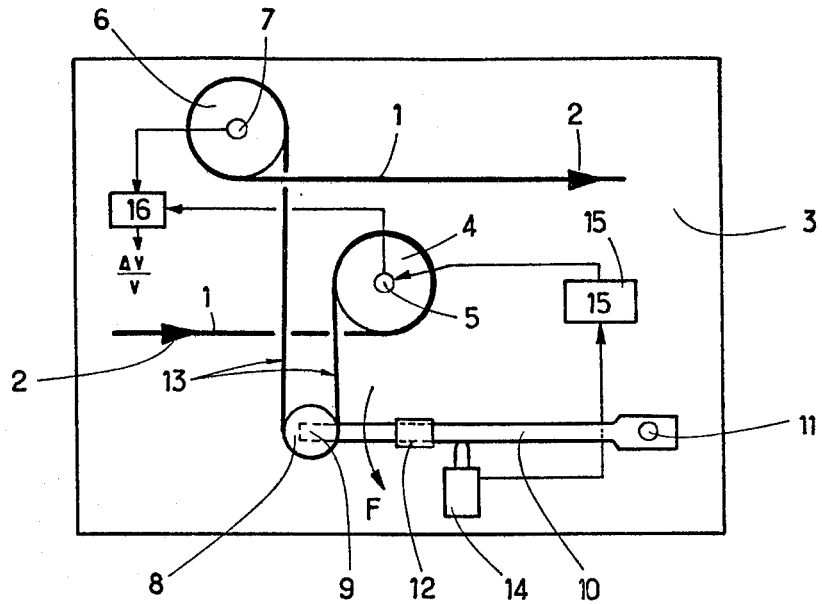
FIGS. 1 and 2 are diagrams of apparatus for continuously measuring the annealing level on wires.
Figure 3:
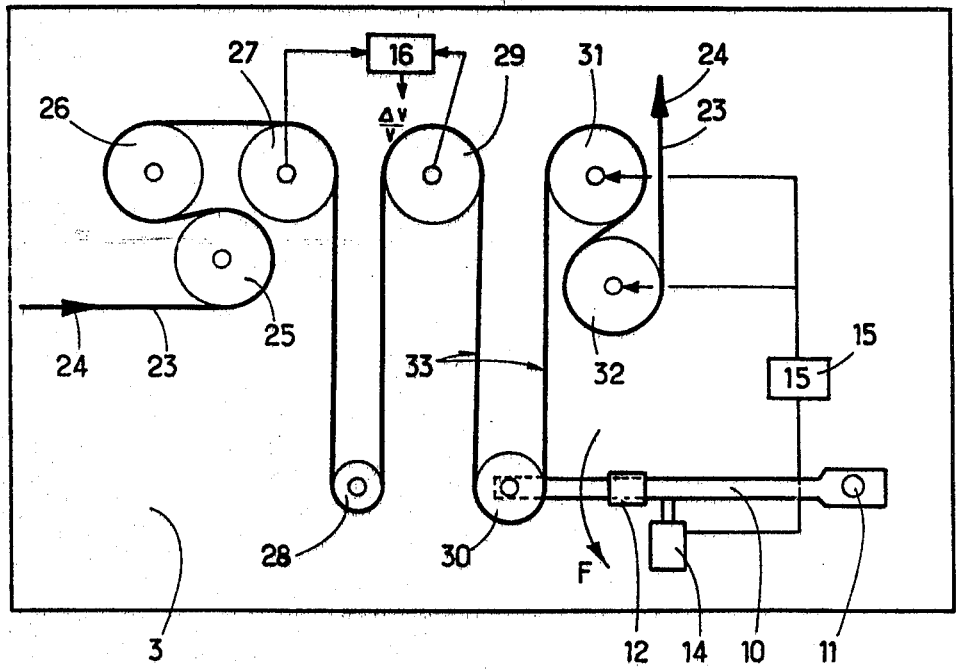
FIG. 3 is a diagram of apparatus for continuously measuring the annealing level on strip.

FIGS. 1, 2 and 3 show three examples of apparatus for carrying out this method. In the first two figures the wire is represented by reference 1 and arrows 2 show the direction in which it advances continuously.

The FIG. 1 apparatus comprises a supporting plate 3 with shafts rigidly connected to it and capstans rotating about the shafts. An upstream capstan 4 is driven by a shaft 5 and a downstream capstan 6 by a shaft 7. The wire 1 is wound around these two capstans without creep.

Between the two capstans the wire 1 passes over a pulley 8 of small diameter rotating loosely on a shaft 9. The shaft 9 is mounted at the free end of a rocker arm 10 which may pivot about a shaft 11 fixed on the supporting plate 3. The arm is acted on by a force F which may be produced by a load 12 hung from it. Wire or strip 1 passes successively over upstream capstan 4, loose pulley 8 and downstream capstan 6, forming a loop 13 to permit free displacement of rocker arm 10.

Force F produced e.g. by load 12 acts on rocker arm 10 and thus on loose pulley 8 mounted at its free end. The force applies the desired mechanical tension to wire or strip 1. A position detector 14 makes it possible to record the position of arm 10 and to control a means 15 for adjusting the rotary speed of the upstream or downstream capstan. Thus it is possible to keep loose pulley 8 in a correct average position, whatever the elongation of the wire, by changing the speed of one of the two capstans according to the position of arm 10.

Each of the capstans has two functions:

1. to allow the wire to be subjected, between them, to strong mechanical tension, close to its elastic limit, without the tension being transmitted upstream or downstream of the capstans;

2. to ascertain the linear speed of the wire before and after elongation on the loose pulley (this is done by measuring their rotary speeds); the relative difference $\Delta v/v$ between the two speeds is automatically calculated in a computer 16 and conveys the relative elongation of the wire during its passage over loose pulley 8.

It should be noted that several of the functions described above can usefully be combined with comparable functions existing in a continuous annealing installation, thus simplifying the construction of the whole unit. For example:

— annealing ovens frequently have capstans for stabilizing the speed of the wire; one of these members may act as the upstream or downstream capstan;
— the rotary speed of the capstans of the annealing oven is frequently measured for the purpose of controlling the intensity of the annealing current; this measurement may be used in calculating the relative difference between the speeds of the two capstans;
— the loose pulley 8 acts as an accumulator to adjust the speed of the wire, a function already provided at the outlet from the annealing ovens.

An example of an improved embodiment is illustrated in FIG. 2.

Wire 1 advances in the direction of arrow 2 and passes successively over upstream capstan 4, around which it is wound (capstan 4 being driven by shaft 5 fixed onto supporting plate 3), then over a pulley 17 of normal diameter, that is to say, considerably larger than that of pulley 8 (pulley 17 turning loosely on a shaft 18 mounted on the free end of rocker arm 10, which is pivoted at its other end on shaft 11 rigidly connected to plate 3), and finally over downstream capstan 6, around which it is wound (capstan 6 being driven by shaft 7 which is likewise fixed to plate 3). The position of arm 10 is recorded by position detector 14.

Located between upstream capstan 4 and loose pulley 17, the arrangement also includes the pulley 8 of small diameter, mounted loosely on shaft 9, which this time is fixed on supporting plate 3. Pulley 8 is preceded and followed by two low-inertia measuring pulleys, pulley 19 on shaft 20, mounted between upstream capstan 4 and pulley 8, and pulley 21 on shaft 22, mounted between pulley 8 and pulley 17. Shafts 20 and 22 are mounted on supporting plate 3, and pulley 21 must be able to turn very freely about its shaft 22. The wire is wound around pulley 8.

Rocker arm 10 supporting loose pulley 17 is subjected to a preset force F, e.g. by the action of load 12 which, when transmitted to the shaft of pulley 17, enables the desired tension to be applied to wire 1. Detector 14 of the position of rocker arm 10 makes it possible to control the automatic adjustment of the speed of the upstream capstan 4 or downstream capstan 6. Thus loose pulley 17 can be kept in a correct average position, whatever the elongation of the wire, by changing the speed of one of the two capstans as a function of the position of the arm. The capstans make it possible for a strong mechanical tension to be applied to wire 1 in the measuring zone, without the high tension being transmitted upstream and downstream of the capstans.

Loose measuring pulleys 19 and 21 make it possible to measure the linear speed of the wire before and after its elongation; it is elongated by passing over pulley 8 of small diameter, which in this example is no longer fixed to the end of rocker arm 10. Thus the measurement is taken under conditions of great reliability since all the parameters are well known.

In particular, the mechanical tension of wire 1 when it passes over pulley 8 is well known, for low-inertia pulley 21, turning freely on its shaft, faithfully transmits the mechanical tension applied by pulley 17, which is subjected to preset force F. The measurement of the elongation of wire 1, carried out by measuring the speed ratio of pulleys 19 and 21, is independent of the amount of creeping of the wire over capstans 4 and 6. There is no creeping over measuring pulleys 19 and 21, for the mechanical tension of the wire is substantially the same on either side of these pulleys.

A known electronic computer 16 (dividing module) converts speed ratio of the two pulleys into an electric signal which can be used for continuously displaying the annealing level obtained and also for controlling that level by feed-back to the generator supplying the electric current for annealing.

The method applies equally to thin strips and even to thick strips intended for embossing, and the apparatus shown in FIG. 3 applies more particularly to this possibility.

The suitability of brass plates continuously annealed in a continuous furnace for embossing depends on the size of the grains of annealed metal. This in turn is closely linked with the annealing level and thus with the mechanical properties revealed in the process described above.

Strip 23 advances in the direction of arrow 24. It is wound successively over a unit of two upstream capstans 25 and 26 forming an S-shaped block, a measuring drum 27, a drum 28 of small diameter fulfilling the same function as pulley 8 in the previous examples, a second measuring drum 29, a drum 30 mounted at the free end of rocker arm 10, and a unit of two downstream capstans 31 and 32 forming a second S-shaped block. Arm 10 can rock about shaft 11; it is acted on by a force F produced e.g. by a load 12 hung over it. Position detector 14 records the position of arm 10; it controls the rotary speed of one of the capstan blocks 25-26 or 31-32. All the capstans can turn around shafts mounted on a supporting plate 3, except for capstan 30 which can be displaced with the free end of arm 10 due to the loop 33 formed by metal strip 23.

Operation is identical with that described above in connection with example 2: capstans 4 and 6 are simply replaced by capstan blocks 25-26 and 32-32 because of the need for accurate feeding of strip 23.

With the aid of computer 16, the relative speed difference between measuring capstans 28 and 29 provides a signal representing the annealing level of strip 23.

If pulley 8 and capstan 28 are small enough in diameter to cause elongation of wire 1 or strip 23, it is obviously preferable for the other pulleys and capstans to have diameters large enough not to produce any deformation of the wire or strip.

Figure 4:
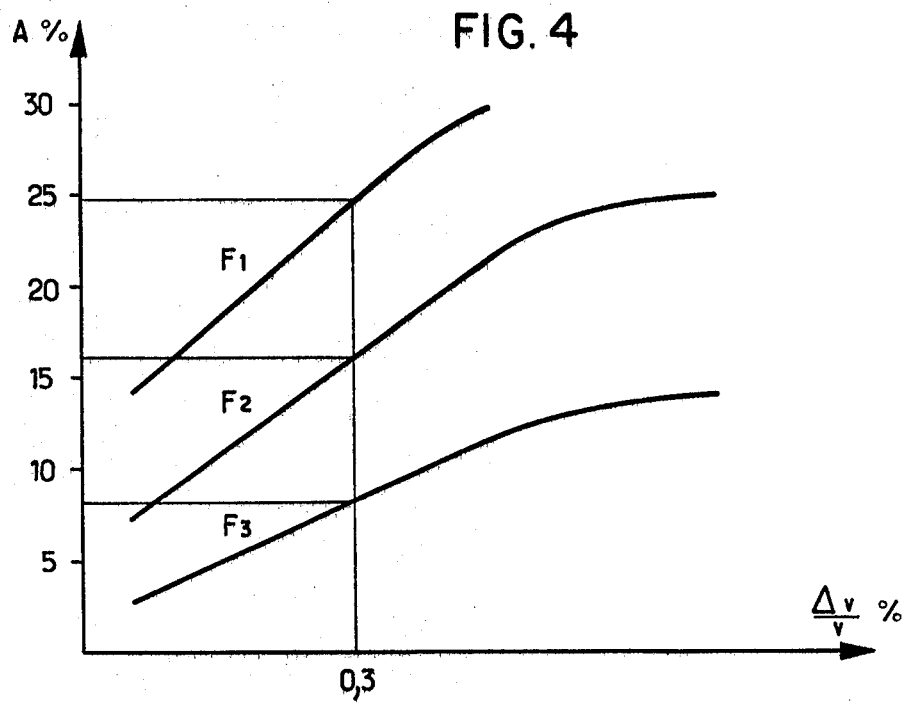
FIG. 4 shows the curves for elongation at rupture A% measured on continuously annealed samples of an aluminum wire 0.5 mm in diameter, as a function of the ratio $\Delta v/v$, the relative difference in speed between the measuring pulleys of the FIG. 2 apparatus, for three increasing values F1, F2 and F3 of the load applied to the rocking arm.

FIG. 4 represents the curves for elongation at rupture A% measured on continuously annealed samples of an aluminum wire 0.5 mm in diameter, as a function of the ratio $\Delta v/v$, the relative difference in speed between two measuring pulleys 19 and 21 in the FIG. 2 apparatus, observed during the corresponding annealing process, for three increasing values F1, F2, and F3 of the load applied to rocker arm 10.

500 kg of this wire is produced, the desired elongation level A% is approximately 25% with a minimum of 20%, and $\Delta v/v$ is chosen as 0.3%. The values for elongation at rupture A%, taken on a basis of 200 mm and measured on 128 samples taken in 10 reels of wire, are from 21 to 29% with a distribution shown in the histogram in FIG. 5. This result, which is appropriate for normal production of aluminum wire, is quite impossible to obtain with a conventional annealing oven not equipped with means for measuring the annealing level, and is better than what can be obtained, other conditions being equal, with the apparatus mentioned above.

FIG. 6 shows the curves for elongation at rupture A% measured on continuously annealed samples of a copper wire 0.8 mm in diameter, as a function of the ratio $\Delta v/v$ observed during the corresponding annealing process, for three increasing values F1, F2 and F3 of the load applied to rocker arm 10 of the FIG. 2 apparatus.

The apparatus shows no tendency to lack of balance, and the correlation between A% and $\Delta v/v$ is excellent, whatever level of annealing is required.

Tests carried out with the FIG. 3 apparatus on a thick brass strip intended for embossing show the perfect correlation between the values of $\Delta v/v$ measured with the apparatus and the grain size of the metal. It is possible for the quality of treatment given in the annealing oven to be continuously checked and for the temperature of the oven to be adjusted accordingly.

The invention applies to continuous, non-destructive testing of any physical or mechanical property or characteristic liable to be connected with the annealing level of any material in the form of a wire or a thin or thick strip.

What is claimed is:

1. An apparatus for continuously measuring and adjusting the annealing level on wire or the like comprising, at the discharge end of a continuous annealing installation, an upstream capstan, a freely rotating pulley of a diameter smaller than said upstream capstan downstream of the upstream capstan, a pivotally mounted arm, said arm including a free end mounting said pulley, means for applying a force to said arm tending to bias said arm and pulley in a first direction, a downstream capstan, means for controlling the speed of one of the capstans in response to the position of the arm, the wire or the like passing successively over the upstream capstan, the arm mounted pulley to the side thereof toward which the pulley is biased, and the downstream capstan, the diameter of the pulley and the tension in the wire as it moves thereabout being such so as to effect a permanent elongation of the wire or the like as it passes about the pulley and means responsive to the difference in relative speed of the capstans, effected by the elongation of the wire or the like therebetween, for use in adjusting the annealing level.

2. The apparatus of claim 1 wherein the diameter of the pulley is from 20 to 500 times the diameter of the wire or the like.

3. The apparatus of claim 1 wherein the diameter of the pulley is from 30 to 200 times the diameter of the wire or the like.

4. An apparatus for continuously measuring and adjusting the annealing level on wire or the like comprising, at the discharge end of a continuous annealing installation, in sequence an upstream capstan, a first measuring pulley, a wire elongating pulley of a diameter smaller than said upstream capstan, a second measuring pulley, a tensioning pulley, and a downstream capstan, means for applying a biasing force to said tensioning pulley, means for adjusting the rotary speed of one of said capstans, a position detector associated with said tensioning pulley and responsive to movement thereof to control the means for adjusting the rotary speed of one of said capstans, the diameter of the wire elongating pulley and the tension produced by the tensioning pulley combining so as to effect a permanent elongation as the wire or the like passes about the wire elongating pulley, the elongation of the wire or the like producing a difference in the relative speed of the measuring pulleys, and means for sensing the difference in the relative speed of the measuring pulleys for controlling the annealing level.

5. The apparatus of claim 4 wherein the diameter of the wire elongating pulley is from 20 to 500 times the diameter of the wire or the like.

6. The apparatus of claim 4 wherein the diameter of the wire elongating pulley is from 30 to 200 times the diameter of the wire.

7. The apparatus of claim 4 including an elongated arm mounted for pivotal movement, said tensioning pulley being freely rotatably mounted on said arm for pivotal movement therewith.

8. An apparatus for continuously measuring and adjusting the annealing level on strips comprising an upstream capstan unit, a first measuring drum, a freely rotating drum of a diameter smaller than said upstream capstan, a second measuring drum, a strip tensioning drum, and a downstream capstan unit, means for applying a position adjusting force to said tensioning drum, means for sensing the position of the tensioning drum and adjusting the rotary speed of one of the capstan units in response thereto, the diameter of the freely rotating drum and the tension applied by the tensioning drum being such so as to effect a permanent elongation in the strip as it passes about the freely rotating drum, said measuring drums sensing the elongation, and means responsive to the sensed elongation for controlling the annealing level.

9. The apparatus of claim 8 wherein the diameter of the drum is from 20 to 50 times the thickness of the strip.

10. The apparatus of claim 8 wherein the diameter of the drum is from 30 to 200 times the thickness of the strip.

11. An apparatus for continuously measuring and adjusting the annealing level on wire or the like comprising spaced upstream and downstream capstan means, a rotating deforming member positioned between said capstan means, means between said capstan means for applying a tension to the wire or the like less than that corresponding to the elastic limit thereof and simultaneously controlling the speed of at least one capstan, the configuration of the deforming member being such so as to, in conjunction with the applied tension, cause a permanent elongation of the wire or the like within a predetermined range, and means responsive to the difference in relative speed of the capstans, effected by the elongation of the wire or the like therebetween for sensing the elongation and controlling the annealing level in response to said elongation.

12. The apparatus of claim 11 wherein said deforming member comprises a freely rotating pulley.

* * * * *